United States Patent [19]

Weissman

[11] Patent Number: 4,976,625
[45] Date of Patent: * Dec. 11, 1990

[54] INHERENTLY NONROTATING RECIPROCATING DENTAL TOOL

[76] Inventor: Bernard Weissman, 225 E. 48th St., New York, N.Y. 10017

[*] Notice: The portion of the term of this patent subsequent to Sep. 4, 2007 has been disclaimed.

[21] Appl. No.: 220,870

[22] Filed: Jul. 18, 1988

Related U.S. Application Data

[63] Continuation-in-part of Ser. No. 179,332, Apr. 8, 1988.

[51] Int. Cl.⁵ .............................................. A61C 1/07
[52] U.S. Cl. ..................................... 433/118; 433/80; 433/166
[58] Field of Search .................. 433/80, 82, 87, 90, 433/118, 119, 120, 121, 122, 123, 124, 125, 128, 165, 166; 222/92

[56] References Cited

U.S. PATENT DOCUMENTS

| | | | |
|---|---|---|---|
| 2,300,828 | 11/1942 | Goldenberg | 433/166 |
| 3,930,173 | 12/1975 | Banko | 433/119 |
| 4,021,917 | 5/1977 | Nakanishi | 433/126 |
| 4,173,828 | 11/1979 | Lustig et al. | 433/122 |
| 4,266,933 | 5/1981 | Warden et al. | 433/82 |
| 4,781,589 | 11/1988 | Bareth | 433/122 |

Primary Examiner—John J. Wilson
Attorney, Agent, or Firm—Paul J. Sutton; Barry G. Magidoff; Anthony Amaral, Jr.

[57] ABSTRACT

There is provided a dental tool for use with a reciprocating drive means and a sleeve member operatively connected to the drive means for reciprocating motion and designed to retain a dental tool, the dental tool comprising a crank portion designed to be retained for reciprocating movement by the sleeve member of the handpiece, and a dental blade, preferably with an abrasive surface, secured to one end of the shank; in one embodiment, the dental tool is preferably hollow and further comprises an axially extending channel, preferably extending along the full length of the shank and a plenum extending within the dental blade, and outlet perforations from the plenum extending through the blade, and in a second embodiment there is further provided means secured to the shank portion for applying pressure within the channel to force any fluid material within the channel and plenum out through the outlet perforations through the blade. Finally, there is provided means for dispensing fluid material, e.g., a cleaning paste, into the shank channel comprising syringe means having a reservoir into the shank of the tool. Preferably, the tool further comprises rotation restraining means, such as an elastically deformable stop member, for providing limited resistance to rotation of the dental tool while it is being subjected to reciprocating motion and the application of axial force during dental therapy.

13 Claims, 6 Drawing Sheets

INHERENTLY NONROTATING RECIPROCATING DENTAL TOOL

BACKGROUND OF THE INVENTION

This is a continuation-in-part of copending application Ser. No. 179,332, filed on Apr. 8, 1988.

The present invention relates to a motor-driven, reciprocating dental tool which inherently improves the means to safely prevent undesirable rotation of the tool during use and further provides sanitary means for simultaneously applying a fluid medium, such as dental cleaning paste, to teeth while mechanically treating, such as cleaning or polishing the teeth by abrasion, and more particularly while mechanically providing axial reciprocating motion to an abrasive member through which the fluid paste is simultaneously applied.

There has previously been successfully provided a mechanically driven hand tool, which can be readily powered by a conventional rotary dental drill, to provide reciprocating motion of the type preferably used when abrading or filing teeth or removing excess restorative material, such as hardened dental amalgams or dental composite materials. Such abrasive methods, depending upon the hardness of the abrasive material and the rapidity and pressure with which the abrading surface is applied, can be used to either remove hardened amalgam or dental enamel or to merely remove plaque and to clean and polish teeth surfaces, including both the major lingual and facial surfaces of teeth as well as the proximate faces bordering the teeth interspaces.

The reciprocating handpiece, such as the device described in U.S. Pat. No. 3,552,022 to Axelsson, and commercially available as a Dentatus EVA Reciprocating Motor Driven Handpiece, has been used for both purposes, together with the dental abrasive tools formed of, e.g., hardened or diamond coated metal blades or plastic blades with or without embedded abrasives. Such handpieces are designed to be driven by a common dental rotary drill driver, and convert the rotary motion of the driver to reciprocating motion through an eccentrically rotating member and a sleeve having a vertically extending groove within which the eccentric rotates, reciprocally moving the sleeve and the blade held by the sleeve, in an axial direction.

It is also known to utilize a syringe type of device to apply toothpaste and the like material for dental hygienic cleaning prior to application of either a mechanically driven or manually operated tooth cleaning means, whether for clinical use or for home use. Such a device is shown, for example, in U.S. Pat. No. 4,411,623 to Axelsson.

SUMMARY OF THE INVENTION

It is an object of the present invention to restrain rotation of an axially reciprocating dental treatment blade under normal therapeutic force, so as to permit accurate positioning and manipulation of the tool, while preventing injury from the accidental application of excessive force. It is also an object of this invention to reduce the number of parts without reducing the important functions of the device, and to provide a tool which can be formed sufficiently economically as to be disposable after a single use, thus further reducing any risk of contagious infection.

It is a further object of the present invention to provide a rotationally restrained reciprocable blade having refillable means for applying a cleaning or abrading fluid or other therapeutic medium to teeth during operation with a mechanically driven tool.

A first aspect of the present invention comprises a mechanically driven reciprocating dental handpiece comprising a blade-holding sleeve reciprocally held within the handpiece, an outer surface of the sleeve being in juxtaposed relationship with an internal surface of the handpiece. There is formed, extending into and beneath the outer surface of the sleeve, a vertically extending notch and on the inner surface of the handpiece a protrusion designed to fit within the notch in the sleeve. The protrusion can be formed by, e.g., a small sphere embedded within the inner surface of the handpiece.

In a most preferred embodiment of this invention, the fluid dispensing and reciprocating abrading tool of the present invention is formed integrally with a shank portion designed to be juxtaposed within a handpiece and to be directly driven by the eccentric driver, while being restrained from rotation during operation by the combination of a protrusion and a groove on the handpiece and on the tool shank. Perferably, the protusion is from the interior of the handpiece and the groove is in the tool shank.

BRIEF DESCRIPTION OF THE DRAWINGS

Preferred embodiments of this invention are further described below, by way of example and not exclusion, by reference to the accompanying drawings which display certain portions of the present invention in schematic form. The details of such schematically shown portions will be readily known to those skilled in the art based upon the following verbal descriptions. Referring to the drawings.

DETAILED DESCRIPTION OF PREFERRED EMBODIMENTS

The dental tool of the present invention is to be used and applied in combination with a conventional commercially available drive head, or handpiece, which is improved in accordance with the present invention. Such a drive head comprises conventional driving elements which do not, in themselves, form a part of the present invention and, thus need not be illustrated in great detail. Examples of suitable driving means are shown, for example, in U.S. Pat. No. 3,552,022 to Axelsson and U.S. Pat. No. 4,629,426 to Levy. Such a device is generally of a sufficiently slender and elongated nature, often having a contra-angle head, to enable a dentist to easily and without injury to the patient, manipulate the device within the mouth and, most particularly, against even the rear molars. However, as such a device is conventional, it will not be described herein in greater detail than is shown in the drawings and can be fully determined from the prior disclosures.

Figure 1:
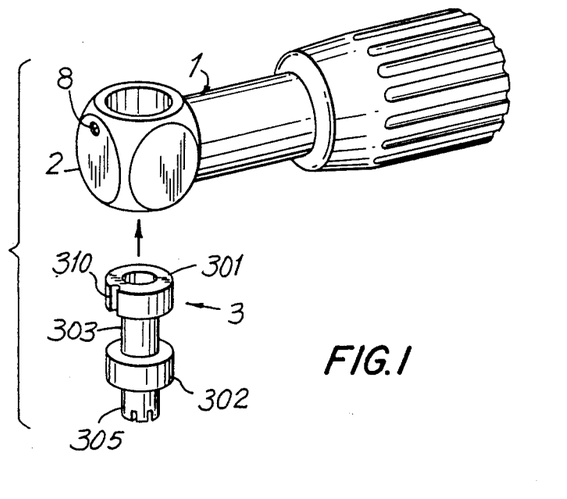
FIG. 1 is a partially exploded isometric view of a file tool-holding sleeve in a reciprocating driver handpiece.
Figure 1A:
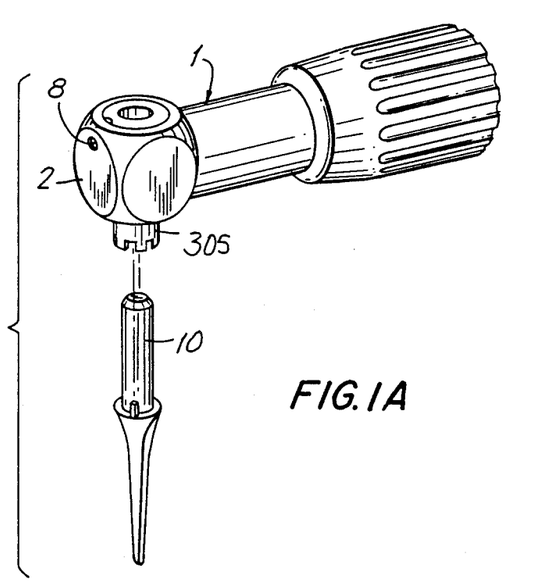
FIG. 1A is a partially exploded isometric view of a file tool held in a sleeve in a reciprocating driver handpiece.
Figure 2:
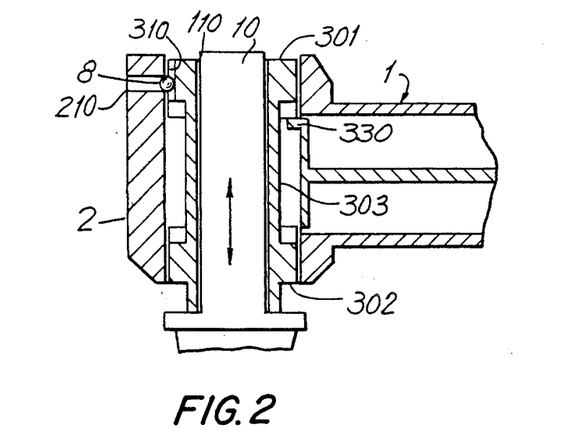
FIG. 2 is a cross-sectional view of the handpiece of FIG. 1.
Figure 3:
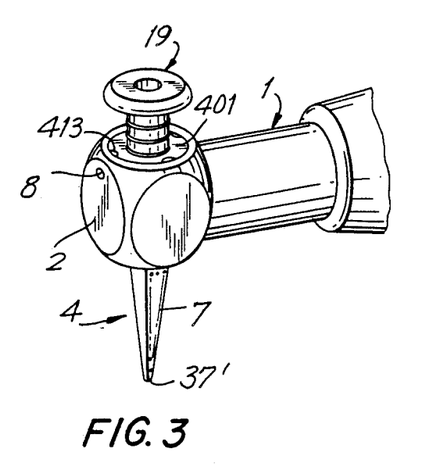
FIG. 3 is an isometric view showing another embodiment of a rotationally restrained, fluid dispensing file blade in accordance with the present invention and the head of a reciprocating dental handpiece.

Referring to FIGS. 1, 1A and 2, a motion-converting, tool-holding sleeve 3 is reciprocatingly held within a head 2 of a dental handpiece, generally indicated by the numeral 1, which converts the rotary motion of the driver mechanism to the desired reciprocating movement. The tool holding sleeve 3 is formed generally cylindrical in shape, having an enlarged flange at the top and adjacent the bottom end. The sleeve 3 defines a bore (defined by internal surface 110) within which the tool shank 10 is held.

The lower and upper large diameter flanges 301, 302 fit securely, but slidably, within the head 2 of the handpiece 1. A vertical groove, or notch, 310 is formed along the upper flange 301. The distance between the two large diameter flanges, i.e. the height of the smaller diameter central portion 303, is sufficient to hold the full stroke of the eccentrically rotating drive member 330 of the handpiece 1. The height of the upper flange 301 and the length of the notch 310, is at least equal to the axial stroke of the sleeve 3. Extending below the lower flange 302 is the notched rim portion 305, which acts to restrain from rotation the blade tool, generally identified by the numeral 4, as described and explained more fully in copending application Ser. No. 179,332.

Formed into the inner surface of the head 2, juxtaposed opposite the vertical notch 310, is a channel 210. Embedded into the channel 210, and protruding into the channel 31, within the head 2, is a steel sphere 8. When the sleeve 3 is inserted in place within the head 2, the steel sphere 8 protrudes into the vertical notch 310, thereby restraining the sleeve 3 from rotating.

Referring to FIGS. 3 through 14, in the preferred embodiment of this invention, the dental tool blade is formed integral with the motion converting sleeve. The entire tool blade, generally indicated by the numeral 4, can be formed as by molding. The tool blades can be formed of polymers or elastomers, such as polypropylene, silicone rubber, or polyurethane. In these preferred embodiments the entire hollow tool 4 (as described and explained more fully in the copending application Ser. No. 179,332), including the sleeve-shank 100 and the blade spine 8 and the blade 7, together with the interior spaces, and perforations, are formed integrally, as by molding procedures well known to the art.

If desired the entire unit can be formed of a single material. Alternatively, by procedures well known to the molding art, portions of the unitarily molded piece can be formed of different materials having properties most useful for each portion; for example, the blade can be formed of a relatively flexible material, whereas the shank can be a relatively hard and inflexible material, except for the surfaces defining the notches, or grooves, into which the protrusion 8 in the head 2 is fitted. The groove surfaces can be relatively soft to permit release of the protrusion 8 when the blade 7 is subjected to excessive force.

The blade portion of the dental tool, generally indicated by the numeral 7, in one preferred embodiment, is elongated, pointed and flat in cross-section, such that a longitudinal but slanted edge 28 is formed between the two major surfaces 27 of the blade 7. The tool, including both the shank 10 and stiffening spine 8 and the blade 7, is hollow to provide a reservoir and channel for the passage of fluid material. As shown, the stiffening spine 8 of the blade 7 does not extend to the end of the blade; the flat blade portion 7 extends both longitudinally and laterally outwardly from the spine 8. The blade 7 has substantially parallel sides 27, although the sides 27 can be slightly convergent towards the edge 28, if desired. Along the blade edge 28 and the blade side surfaces 27, are provided perforations 18 extending fully through the blade material and into the interior hollow space, defined by the interior surfaces 17 within the blade 7. This interior space 17 is directly open to the hollow channel defined by shank channel surfaces 16 extending to the top of the shank 100. Preferably, the minimum width at the blade edge 28 should not be less than about 0.01 in., if outlets 18 are provided at the edge 28, in order to provide sufficient interior space for passage of a fluid.

The material forming the shank 100 is molded integral with the blade 7 in the form shown in the drawings. Two relatively large diameter flange portions 401, 402 are formed at the top of the tool and at the top of the blade portion 7, respectively. Intermediate the two flanges 401, 402 is a smaller diameter neck portion 403 designed to mate with the eccentrically rotating driver member (not shown in this drawing). The upper flange 401 is formed with four vertically extending grooves or notches 413, designed to match with the head protrusion, such as the steel sphere 8 embedded in the inner surface of the head 2. The upper flange 401 is further split horizontally by a circumferential groove 423, which preferably is not as deep as the vertical grooves 413, to permit rotation of the blade from one groove 413 to another, to change the relative angle of the blade.

A pressure feed cap, generally indicated by the numeral 19, is formed integral with the tool via a strap 29 extending from the top of the flange 401 intermediate two of the vertical notches 413. The cap 19 comprises a plunger 13, and a larger diameter outer button 39 secured thereto and having a flat outer surface. The plunger 13 also includes circumferential ridges 15. The plunger 13 creates a piston action as it is pressed into the channel 416 by finger pressure on the cap outer surface 39. The outer cap surface 39 preferably is shaped and textured for improved fingertip control.

The manner of driving the reciprocating integral blade of this invention can be the same as is shown, for example, in U.S. Pat. Nos. 3,552,022 or 4,629,426.

The tool is preferably formed of a polymer or elastomer and the thickness of the walls 27 of the blade 7 is preferably not greater than about 0.015 in. and most preferably in the range of from about 0.005 to about 0.01 in. This thickness, together with the reinforcing spine 8, is sufficient to prevent excessive flexibility or folding during use of the major part of the blade, whereas the outer point 37 is of greater flexibility as it extends beyond the end of the spine 8. Such thin, flexible blade is well adapted to being inserted into the dental interspaces for e.g., polishing, cleaning, abrading and shaping, or applying medication.

The major surfaces 27 and leading edge 28 of the tool blade 7 can be formed so as to provide a desired effect. For example, the major surfaces 27 can be formed with a rough grainy surface, or with embedded particles of a harder material than the polymer or elastomer, or even molded with tiny fibers, or tendrils, on the surface, e.g., in the manner in which a so-called Velcro surface is formed.

Figures 15, 16:
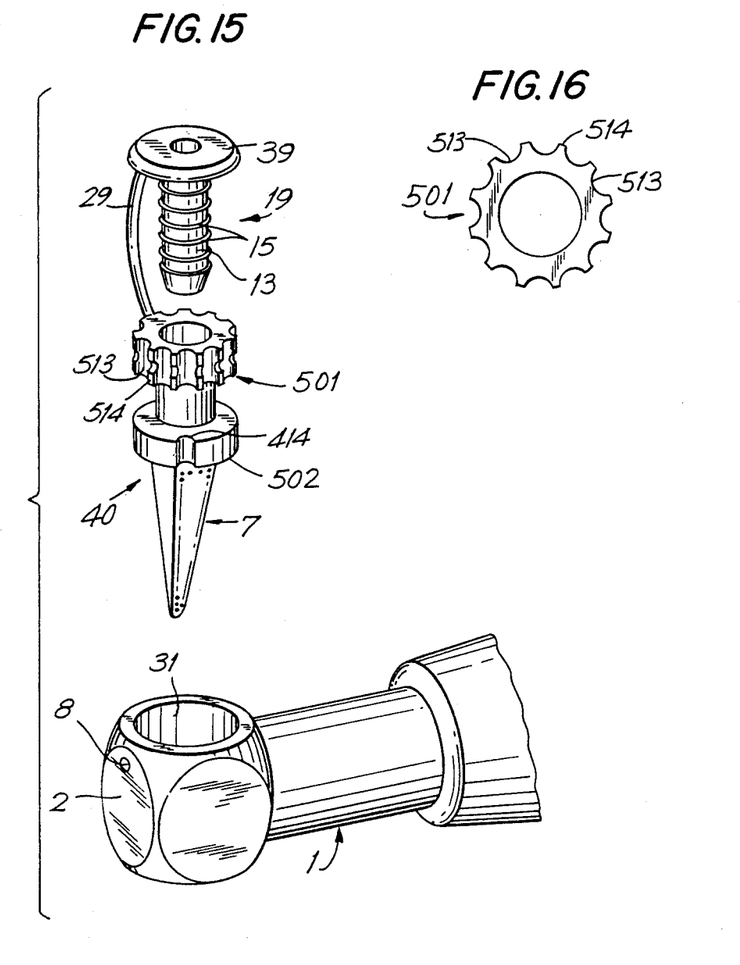
FIGS. 15 and 17 are exploded isometric views showing further embodiments of the integral blade tool of the present invention.
FIG. 16 and 18 are top views of the blade tools of FIGS. 15 and 17, respectively.

In another alternative embodiment, as shown in FIGS. 15 and 16, the unitary tool, generally indicated by the numeral 40, is formed with an upper flange 501 having a larger number of vertical rotation-restraining notches 513, separated by thinner sections of material 514. The juxtaposition of a particular groove 513 with the head inner protrusion 8, determines the angular relationship between the surfaces of the blade 7 and the centerline of the handpiece 1. Thus, by increasing the number of notches 513, the angular relationship can be more finely controlled.

Figure 4:
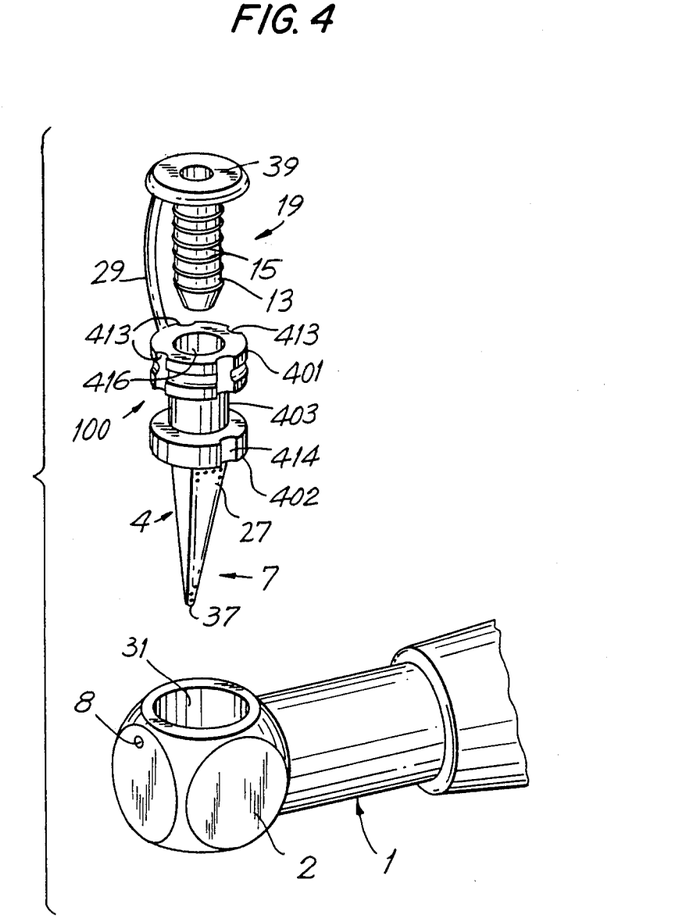
FIG. 4 is an exploded view of the device of FIG. 3.
Figure 5:
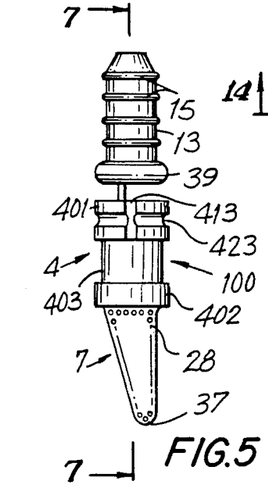
FIG. 5 is a side elevation view of the tool of FIG. 4.
Figure 6:
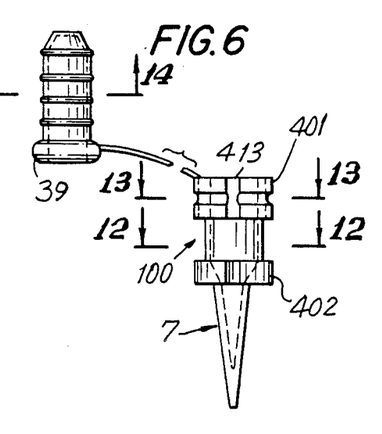
FIG. 6 is another side view of the tool of FIG. 4.
Figure 7:
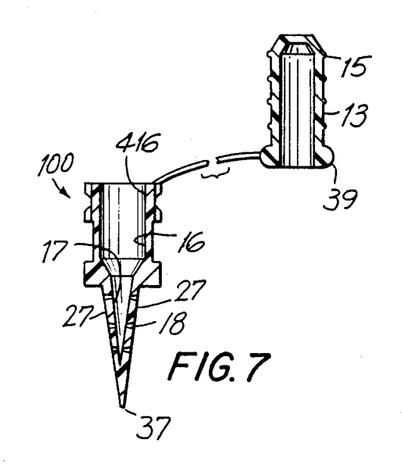
FIG. 7 is a sectional view taken along lines A—A of FIG. 5.
Figure 8:
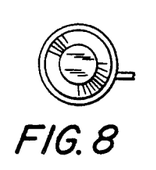
FIG. 8 is a top view of the cap of FIG. 6.
Figure 9:
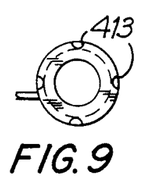
FIG. 9 is a top view of the tool of FIG. 6.
Figure 10:
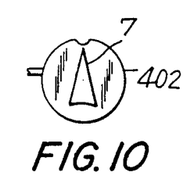
FIG. 10 is a bottom view of the tool of FIG. 6.
Figure 11:
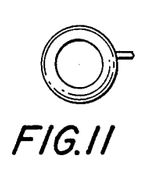
FIG. 11 is a bottom view view of the cap of FIG. 6.
Figure 12:
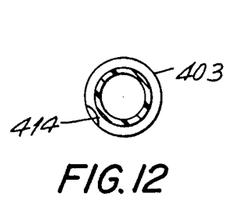
FIG. 12 is a cross-sectional view taken along lines D—D of FIG. 6.
Figure 13:
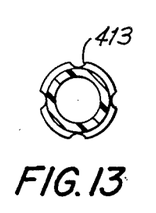
FIG. 13 is a cross-sectional view taken along lines C—C of FIG. 6.
Figure 14:
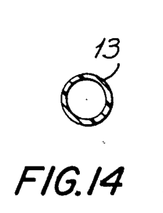
FIG. 14 is a cross-sectional view taken along lines B—B of FIG. 6.

In addition, by having thinner separating walls 514 between the notches 513, there is also provided greater control over the releasing force, than for the relatively thick walls of the embodiment of FIG. 4. Specifically, by varying the flexural modulus of the walls, i.e., by selecting a suitable material of construction, the release force can be varied over a wide range, depending upon for example, the age and health of the patient being treated, and the treatment being given.

The dental tool 4, 40 of this invention can be filled with fluid before or after being inserted into the handpiece head 2. When the tool 4, 40 is inserted it can be done from the bottom or the top of the head 2. When being inserted from the top, of course, the largest dimension of the blade must be smaller than the diameter of the lower flange 402, 502; in that case, the lower flange 402, 502 is formed with a vertical notch 414, to enable it to pass over the steel sphere 8. In addition there is preferably a ledge on the inside surface 31 of the head 2, against which the lower surface of the lower flange 402, 502 will abut, to prevent the blade from falling through the head 2; alternatively, a collar can be provided at the top of the upper flange 401, 501 to restrain the tool 4, 40 from falling, or being pulled, out accidentally. When the tool is inserted through the bottom of the head 2, there is preferably a collar around the bottom edge of the lower flange 402, 502, or if the major dimension of the blade is larger than the diameter of the lower flange 402, 502, the upper surface of the blade 7 can serve as a lower restraint.

When the cap 19 is inserted into the channel in the shank 100, it should fit sufficiently snugly to act as a piston when being depressed. It should not, however, cause the shank 100 to expand, as that would interfere with the reciprocating motion of the blade within the head channel 31.

When the tool 4, 40 is in place in the head 2, the steel sphere 8 mates with a flange notch 413, 513. The plunger 13 is lightly inserted into the shank channel 16 and the handpiece power is activated causing the tool 4, 40 to reciprocate. Pressing downwardly against the outer cap surface 39 forces the plunger 13 into the shank channel 416, which causes the paste, or other fluid, previously charged into the tool, to flow out through the perforations 18.

When the blade 7 is inserted into teeth interspaces, the blade surfaces 27 will, e.g., polish the tooth surfaces If the blade 7 becomes lodged, and an excessive rotational moment is exerted, the relatively resilient material defining the notches 513 on the flange 501 can flex and permit the steel sphere to break away out of the notch 513, permitting rotation of the tool and preventing injury to the teeth. For this purpose, the material forming the notch wall should have a suitable flexural elastic modulus and thickness.

Figure 17:
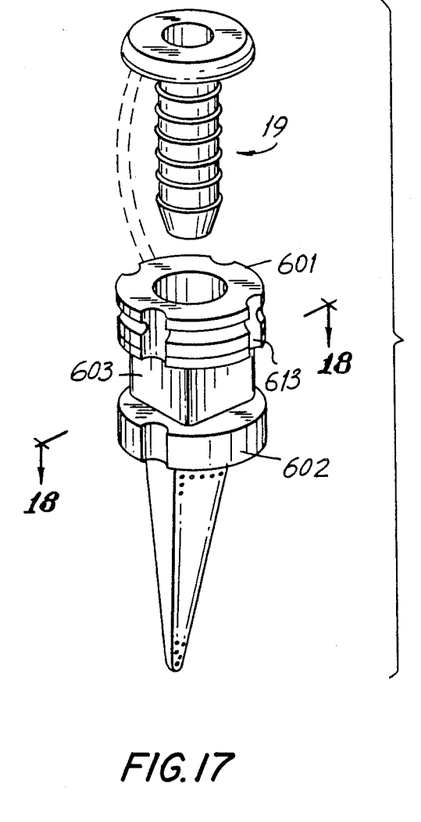
Figure 18:
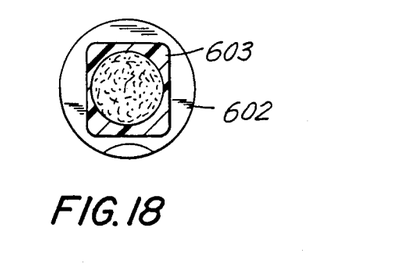

Referring to FIGS. 17 and 18, rotation restraint is also provided by the planar facets 504, of the squared off neck portion, generally indicated by the numeral 503. The corners 507 of the facets are all within the outer circumferences of the two flanges 501,502. The eccentric driver rotates about an axis substantially perpendicular to the plane of each facet 504 between the two flanges 501,502, in the same manner as with the other embodiments described above.

The patentable embodiments which are claimed are as follows:

1. In a dental device comprising a drive head, an internal channel defined within said drive head, reciprocating drive means extending into said internal channel, and designed to provide reciprocating motion to a dental tool, and a dental tool having a shank and a blade portion, said shank portion being retained in said internal channel, the improvement comprising a protrusion extending radially inwardly into the head channel, and wherein the shank is formed integral with the blade and wherein the shank comprises an indented drive portion designed to hold the reciprocating drive means, a flange portion having an enlarged diameter and designed to fit slidably but snugly within the internal channel, and a plurality of grooves along said flange portion extending substantially parallel to the axis of the shank and designed to snugly hold the protrusion from the drive head, the dental tool being thus restrained from rotary motion.

2. The dental device of claim 1, wherein the shank portion further comprises a second flange portion adjacent the blade and wherein the reciprocating drive means moves in the space intermediate the two flange portions.

3. The dental device of claim 1, wherein the dental tool further comprises an internal channel extending axially along a central portion of the shank, and a plenum chamber within the blade portion in fluid flow connection with the shank channel, outlet openings through the blade surface, and pressure means and closure means for the shank channel, operable to force any fluid material within the channel and plenum out through the outlet openings.

4. A dental tool having a shank and a blade portion, the shank being designed to be directly retained in a reciprocating dental tool drive means, the shank comprising a first flange portion at the distal end of the shank from the blade, and a second flange portion proximal the blade, the flanges being designed to fit snugly but slidably within the dental tool drive means, a plurality of axially extending grooves being defined about the perimeter of the first flange and an axially extending groove along the perimeter of the second flange.

5. The dental tool of claim 4, comprising an internal channel extending axially along a central portion of the shank, and a plenum chamber within the blade portion in fluid flow connection with the shank channel, outlet openings through the blade surface, and pressure means and closure means for the shank channel, operable to force any fluid material within the channel and plenum out through the outlet openings.

6. The dental tool of claim 5, wherein the pressure means comprises a plunger cap comprising a piston portion slidably and removably secured within the shank channel and an end cap having a diameter greater than that of the piston portion and extending beyond the shank, the cap being designed to be manually depressed.

7. The dental tool of claim 6, comprising an elongated strap means secured at one end to the cap and at the other end to the shank, whereby the plunger cap is permanently secured to the shank and blade portions of the dental tool.

8. The dental tool of claim 4, wherein there is also defined on the first flange a circumferentially extending groove intersecting the axially extending grooves.

9. The dental tool of claim 8, wherein the depth of the axial groove below the surface of the flange is greater than the depth of the circumferential groove.

10. In a dental device comprising an elongated portion and a head portion at one end of the elongated portion, an internal channel within the head portion open at both ends, rotary drive means within the elongated portion and extending into the channel in a direction transverse to the axis of the channel, a sleeve member slidably held within the internal channel and having an indented portion facing transversely of the axis of the channel and operatively connected to the rotary drive means to convert rotary motion to reciprocating linear motion, and a dental tool having a shank and a blade portion, the sleeve member being designed to retain the shank of the dental tool, the improvement comprising a rigid projection extending outwardly from one of the sleeve member and the head portion, and a concave surface on the other of said sleeve member and head portion, the projection and concave surface being in mating juxtaposition during operation of the dental device to provide restraint against rotation of the sleeve member relative to the drive means; and a flexible projection extending outwardly from one of the dental tool and the sleeve, and a mating concave surface formed on the other of the dental tool and the sleeve, the flexible projection and the mating concave surface being in mating juxtaposition during operation of the dental device to provide limited restraint against rotation of the tool relative to the sleeve.

11. The dental device of claim 10, wherein the flexible projection extends from the shank of the tool adjacent the blade portion, the projection extending longitudinally along the shank and radially outwardly from the shank, and the concave surface is formed on the edge of the sleeve proximal the blade.

12. The dental device of claim 11, wherein the rigid projection extends outwardly from the internal channel of the head portion and the concave surface is formed on the external surface of the sleeve.

13. The dental device of claim 11, comprising a plurality of concave surfaces formed on the proximal end of the sleeve.

* * * * *